United States Patent [19]

Lalezari

[11] Patent Number: 4,780,542

[45] Date of Patent: Oct. 25, 1988

[54] PROCESS FOR THE SYNTHESIS OF ESTERS AND AMIDES OF CARBOXYLIC ACIDS

[75] Inventor: Iraj Lalezari, Scarsdale, N.Y.

[73] Assignee: Montefiore Medical Center, Bronx, N.Y.

[21] Appl. No.: 535,573

[22] Filed: Sep. 26, 1983

[51] Int. Cl.$^4$ .................... C07D 249/18; C11C 1/00; C07C 67/08; C07C 102/00

[52] U.S. Cl. .................... 548/261; 260/404; 260/404.5; 260/405.5; 260/410.5; 260/410.9 R; 260/410.9 N; 260/546; 548/163; 548/268; 560/64; 560/73; 560/98; 560/103; 560/106; 560/204; 560/205; 560/220; 560/221; 560/225; 560/254; 560/261; 560/265; 564/133; 564/144

[58] Field of Search ............ 260/404, 405.5, 410.9 R, 260/410.5, 404.5, 410.9 N, 546; 548/261, 268, 163; 560/80, 81, 82, 64, 73, 84, 85, 86, 95, 98, 100, 102, 103, 105, 106, 107, 108, 109, 113, 121, 122, 127, 130, 138, 139, 141, 146, 193, 194, 201, 204, 205, 220, 221, 225, 249, 254, 255, 261, 265; 564/133, 144

[56] References Cited

U.S. PATENT DOCUMENTS

| | | | |
|---|---|---|---|
| 2,873,292 | 2/1959 | Meyer | 560/98 |
| 4,360,691 | 11/1982 | Perrin | 560/131 |
| 4,487,961 | 12/1984 | Aristoff | 562/501 |

OTHER PUBLICATIONS

Nelson et al., J. Organic Chemistry, vol. 28, pp. 1905–1907, Jul. 1963.

Primary Examiner—Werren B. Lone
Assistant Examiner—Vera C. Clarke
Attorney, Agent, or Firm—Hedman, Gibson, Costigan & Hoare

[57] ABSTRACT

The invention relates to the preparation of an ester or an amide from an anhydride with an alcohol or an amine, wherein the anhydride is first prepared by reacting an acid and an alkyl chloroformate in a 100% aqueous medium, that is, 100% water.

18 Claims, No Drawings

PROCESS FOR THE SYNTHESIS OF ESTERS AND AMIDES OF CARBOXYLIC ACIDS

BACKGROUND OF THE INVENTION

The importance and usefulness of esters and amides as industrial products as well as intermediate for the preparation of compounds having diverse utilities is well known. Esters have been prepared by direct esterification of an alcohol and an acid by reaction of a metallic salt with an acyl halide and by an acid anhydride with an alcohol or the reaction of an acid and alcohol by refluxing in the presence of a suitable dehydrating agent such as concentrated sulfuric acid. These reactions have typically been carried out in the presence of an organic solvent and have generally been regarded as slow reactions usually requiring catalysts. In addition, these reactions are not generally regarded as being capable of producing the desired reaction product in near quantitative yields.

The preparation of mixed carboxylic-carbonic anhydrides and the subsequent conversion of these compounds into amides with ammonia is described by Nelson et al. J. Org. Chem. 28:1905 (1963). This article shows the preparation of amides and esters from a mixed anhydride using an organic solvent as a reaction medium.

It has been discovered that water may be used as the sole reaction solvent for the preparation of esters and amides of fatty acids when the esters and amides are prepared by using a mixed anhydride reaction.

The use of water in this reaction is advantageous because it results in higher yields of the reaction products and facilitates the separation of the product from the reaction mixture.

Therefore it is a primary object of this invention to provide a novel process for the preparation of esters and amides.

It is also an object of this invention to provide a process for the preparation of esters and amides that is carried out in an aqueous system.

These and other objects will become apparent from a review of the following detailed description of the invention.

DETAILED DESCRIPTION OF THE INVENTION

The esters that may be prepared according to the process of the invention includes those of the formula:

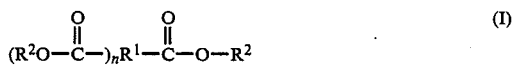

wherein $R^1$ is selected from the group consisting of straight and branched chains alkyl or hydroxyalkyl of from 2-30 carbons; straight and branched chain alkenyl or hydroxyalkenyl of from 2-30 carbons, alkaryl; aralky; aryl; cycloalkyl of from 5 to 7 carbons; alkylene; alkarylenealkyl; and $R^2$ is independently selected from the group consisting of straight and branched chain alkyl or hydroxyalkyl of from 1-30 carbon atoms; straight and branched chain alkenyl or hydroxyalkenyl of 1-30 carbons; cycloalkyl of from 5 to 7 carbons; alkaryl; aralkyl and aryl; n is 1 or 0.

The compounds of formula I when n is 0 are known esters which have known uses. For example ethyl acetate and the liquid esters are used as solvents for coating compositions. The solid esters such as cetyl palmitate may be used as components of lubricating compositions or emollients in cosmetic formulations. The preferred esters are those of normal and fatty acids with aliphatic alcohols of 1-6 carbon atoms or aryl alcohols such as benzyl alcohol.

The term alkaryl is used herein to describe alkyl substituted aromatic groups wherein the alkyl group has from 1 to 6 carbon atoms and the aromatic group is phenyl or naphthyl; the term aralkyl is used to describe groups wherein an aryl group such as phenyl or naphthyl is substituted onto an alkyl group of from 1 to 6 carbon atoms; the term aryl has been used to include phenyl and naphthyl; the term alkenyl is used to include hydrocarbon groups having one, two or three double bonds; the term arylene has been used to include phenylene and naphthylene; and the term alkylene has been used to include $-(CH_2)_m-$ groups wherein m is from 1 to 10. The terms aralkyl and alkaryl are used to include groups which include $-(CH_2)_m-$ aryl; $-(CH_2)_m-$ arylene $(CH_2)_m$; and aryl $(CH_2)_m$ arylene.

The various carbon atoms of $R^1$ also be substituted with halogens such as chloro or bromo.

The process is based on the formation of a mixed anhydride from an acid of the formula:

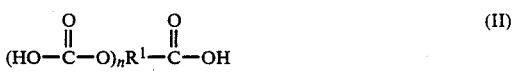

wherein $R^1$ and n are the same as hereinabove defined. This acid is combined with a basic compound and reacted with a chloroformate of the formula $ClCOOR^4$ wherein $R^4$ is alkyl of from 1 to 10 carbon atoms or aryl such as phenyl in an aqueous medium to yield an anhydride intermediate of formula III.

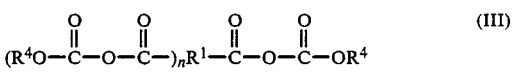

wherein $R^1$, $R^4$ and n are the same as hereinabove defined. This intermediate anhydride then reacts under basic condition with an alcohol of the formula:

wherein $R^2$ and n is 0 or 1 as is above-identified. If n is 1 in formula III and n is 0 in formula IV, a diester will be obtained. When n is 0 in formula III and n is 1, a hydroxyalkyl ester will be obtained.

The basic compound is not critical and may be a tertiary amine such as $N(R^5)_3$ when $R^5$ is an alkyl group of 1-6 carbon atoms; an alkanolamine such as $N(CH_2)_n-OR^5$ wherein $R^5$ is H or alkyl groups and n is 1, 2, or 3, alkali metal hydroxides and alkaline earth metal hydroxides such as NaOH and KOH; $Mg(OH)_2$; $NaHCO_3$; $Na_2CO_3$ or other basic compounds. From 0.5 to 2.5 moles of the basic compound may be used per mole of acid.

The process may be practiced by combining in a suitable reactor, approximately one molar equivalent of an acid of formula II and approximately 1.5 molar equivalents of a basic compound in an aqueous medium that comprises an amount of water that is approximately 0.1 to 20 liters of water per mole of acid. The amount of water is not critical and may vary depending on the acid. For example 2-2.5 liters of water per mole of $C_2$–$C_{15}$ alkanoic or alkenoic acids and from 3–5 liters for $C_{16}$–$C_{18}$ alkanoic or alkenoic acids.

The more difficultly soluble acids require larger volumes of water and the water may be warmed and agitated to facilitate dispersion of the acid. A true solution is desirable but it is not essential for the operation of the process.

The term aqueous medium is used to describe a reaction medium that comprises more than about 70% water and more preferable from about 80 to 100% water. If nessessary to achieve a uniform dispersion of a relatively water insoluble material up to 30% and preferably less of a suitable organic solvent may be utilized to achieve a suitable dispersion of any material that is difficult to dissolve. Suitable solvents include acetone, tetrahydrofuron, dioxane and the like. After the acid is mixed with the water and base, the mixture is cooled to about 0° C. and temperatures lower than about 0° C. down to about the freezing point of the reaction mixture. While the cooled mixture is vigorously agitated, approximately one molar equivalent of an alkyl chloroformate is slowly added. It is preferred to also intermittently add crushed ice with the alkyl chloroformate to control the exotherm but cooling coils, or other temperature control means may also be utilized. The reaction mixture is agitated, preferably by stirring for 0.25 to 3 hours, preferably for about 1.5 hours while the temperature is maintained between 10° C. and the freezing point of the mixture. It has been found that keeping the temperature at about 0° C. gives good results. Thereafter a slight molar excess (1.1–1.5 moles) of an alcohol of Formula II is directly added to the reaction mixture and agitation is continued for 0.1 to 2.0 hours. If the particular alcohol is insoluble in water, it may be dissolved in a small quantity of a suitable organic solvent such as acetone or dioxane prior to adding the alcohol to the reaction mixture.

The reaction mixture containing the ester may be warmed to 40° C.–80° C. for 0.1 to 0.5 hours prior to separating the ester from the reaction mixture. The liquid esters are separated by decantation and/or extraction using conventional techniques.

The amides that may be prepared according to the process of the invention include amides of the formula:

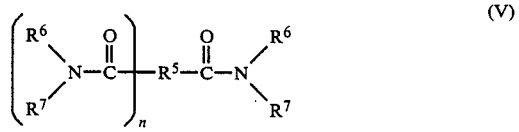
(V)

where $R^5$ is selected from the group consisting of straight and branched chain alkyl, aminoalkyl or hydroxyalkyl of from 1 to 30 carbons; straight and branched chain alkenyl, aminoalkyl or hydroxyalkenyl of from 1 to 30 carbons; aryl; cycloalkyl of from 5 to 7 carbons; alkylene; and arylene; $R^6$ and $R^7$ may be the same or different and are independently selected from the group consisting of hydrogen, straight and branched chain alkyl, aminoalkyl, mono and dialkylaminoalkyl or hydroxyalkyl of from 1 to 30 carbon atoms; straight and branched chain alkenyl or hydroxyalkenyl of from 1 to 30 carbon atoms; aryl; cycloalkyl of from 5 to 7 carbons; alkaryl; aralkyl; 2-benzothiazole; and n is the same as hereinabove defined.

Groups which are included in aminoalkyl are of the formula $CH_3(CH_2)_nCH_2NH_r$—$(CH_2)_n$—wherein n is from 0 to 10; r is 1 or 2 with the proviso that r is only 2 when n is 0; the groups which are included in mono and dialkyla-minoalkyl are of the formula

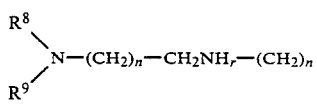

wherein $R^8$ and $R^9$ are independently hydrogen or alkyl of from 1 to 6 carbons; n is 0 to 10 and r is the same as hereinabove described.

The compounds of Formula V are known compounds which in liquid form may be used as solvents such as N,N-dimethylformanide, N,N-dimethylacetamide and the like, and for other well known uses. The solid amides may be used as additives in detergent compositions, in basic solutions and for other well known uses such as derivatives for the identification of carboxylic acids according to the chemical literature or as organic synthesis intermediates.

The amides may be prepared by using the general procedure that has been outlined for the esters hereinabove except that an appropriate amino compound is used in place of the ester. The amides may be separated by filtration of the reaction mixture or by other conventional techniques.

DESCRIPTION OF THE PREFERRED EMBODIMENTS

The following examples are set forth as further descriptions of the invention, but are not to be construed as limiting the invention thereto.

EXAMPLE 1

A solution of 1.722 g. (0.01 mole) of decanoic acid and 1.5 ml triethylamine in 25 ml water was prepared by warming on a water bath. The solution was rapidly cooled in an ice-salt bath while stirring. After the temperature of about −2° C. was reached, 1.0 ml. ethyl chloroformate was slowly added along with about 2 g. of crushed ice. Stirring was continuted for an additional hour (internal temperature was maintained) between 0 and −2° C.). Finally 1.5 ml. benzyl alcohol was added. Stirring of the reaction mixture was continued for ½ hour on a 60° water bath. After cooling, the ester was extracted twice by 30 ml ether, washed with sodium, bicarbonate solution then with water. After drying and evaporation of the solvent, the ester was distilled under reduced pressure to give 2.574 g. (99% yield) of benzyldecanoate. B.P. 208–210/15 mm. Anal. Calcd. for $C_{17}H_{26}O_2$:c, 77.82; H, 9.98. Found: C,77.69; H, 10.03.

EXAMPLE 2

A solution of 2.56 g. (0.01 mole) of palmitic acid and 1.5 ml. triethylamine in 25 ml. water was prepared by slight warming. The solution was rapidly cooled in an ice-salt bath. At temperature about −2° C., 1 ml chloroformate and 2 g. ice was added with stirring. After one hour stirring between 0 and −2° C., a solution of 2.42 g. (0.1 mole) of cetyl alcohol in 30 ml. dioxane was added at once and the ice salt bath was removed. Stirring was continued for ½ hour at room temperature then ½ hour at about 60°. After cooling in ice bath, the PH was adjusted at about 12 by the addition of 5% sodium hydroxide solution to dissolve any unreacted acid. A granular precipitate was obtained which was filtered, washed with cold water and dried. It was recrystallized from dilute methanol to give 4.75 g. (99% yield) of 2-cetyl-palmitate MP 53–54 (lit.: U.S. Pat. No. 3,169,099. 1965 gives MP 54.

EXAMPLE 3

To the mixed anhydride prepared from 2.32 g. (0.02 mole) of hexanoic acid in 5 ml. methanol was added and stirred for ½ hour at room temperature then ½ hour at about 60°. The separation and purification or methyl n-caproate was identical with the method used in Example 1. The ester was distilled at normal pressure to give 2 g. (77%) of methyl-n-caproate b.p. 150 (lit.: Beilstein. Vol. 2, II, 284, b.p. 151/760).

EXAMPLE 4

The mixed anhydride was prepared from 2.83 g. (0.01 mole) of oleic acid as described in Examples 1 and 2.

To the mixed anhydride preparation 10 ml (excess) of 28 per cent ammonia solution was added. After ½ hour stirring at room temperature and ½ hour at about 70°, the reaction mixture was cooled. A crystalline compound was separated which was recrystallized from dilute methanol to give 2.8 g. (100% yield) of 9-cis-octadecenoyl amide mp 74°–76° (lit.: Beilstein Vol. 2, III 1425 mp 76°).

EXAMPLE 5

To the mixed anhydride prepared from 2.32 g. (0.02 mole) of hexanoic acid as described in Example 2., a solution of 3 g. (0.02 mole) of 2-aminobenzothiaole in 10 ml. acetone was added. After stirring for ½ hour at room temperature and ½ hour at about 60° and cooling a crystalline compound was obtained. It was recrystallized from dilute methanol to give 4.2 g. (92% yield) of 2-n-hexanoylamidobenzothiazole mp 145°–146°.

Anal. calcd. for $C_{13}H_{16}N_2OS$: C,62.90; H,6.45. Found: C, 62.88; H,6.42.

EXAMPLE 6

A solution of 2.284 g. (0.01 mole) of myristic acid was converted to its corresponding mixed anhydride derivative, 1.5 ml. (50 percent excess) of 1,1-dimethylamino-3-aminopropane was added and stirred for ½ hour at room temperature and ½ hour at about 60°. The pH was adjusted to 12 by the addition of IN NaOH and it was extracted with ethyl acetate (3×15 ml) The organic layer was washed several times with water and evaporated to give 2.59 g. of N-(3-dimethylaminopropyl) tetradecanoamide (82% yield) mp 44–45.

One gram of base was dissolved in 10 ml. ethanol containing 1 ml. 48% HBr. Addition of 25 ml. acetone gave a white hygroscopic powder which was filtered, washed with acetone and dried in a dessicator. The yield of the HBr salt was 1.25 g. (100%).

Anal. calcd. for $C_{19}H_{44}N_2O.HBr$ Br,20.15. Found Br,20.28.

EXAMPLE 7

To a solution of 1.221 g. (0.01 mole) benzoic acid 1.5 ml. triethylamine in 25 ml. water was cooled in an ice-salt bath. 1 ml. ethyl chloroformate was added (with some ice). After stirring for one hour at about −2°, 1.5 ml. benzyl alcohol was added. Stirring was continued for ½ hour at room temperature and ½ hour at about 60°. An oil was separated which was extracted with ethylene chloride. The organic layer was washed with sodium bicarbonate solution, then with water. After drying it was distilled in reduced pressure (b.p. 180–185/15 min.). The yield was 1.975 g. benzyl benzoate (93%). colorless oil with pleasant odor.

Anal calcld. for $C_{14}H_{12}O_2$; C, 79.23; H, 5.69. Found: C,79.31; H,6.01.

EXAMPLE 8

A mixed anhydride solution is prepared from 1.88 g. (0.01 mole) azelaic acid in 25 ml of water, 4 ml. of trimethyl amine and 2 ml. of ethylchloroformate in a reaction vessel cooled by an ice salt bath. The reaction is carried out for three hours with stirring when 5 ml. of methanol is added. The reaction mixture is stirred for a half-hour at room temperature and a half-hour at about 60° C. The ester is washed with sodium carbonate solution (5%) and purified by distillation. The yield is 1.55 g. (70%).

EXAMPLE 9

The procedure of Example 8 is repeated and at the end 5 ml. of concentrated ammonium hydroxide solution (28% $NH_3$) is added and the amide is separated by cooling of the reaction mixture. The yield is 0.6 g. (30%) mp 171°–173° C.

Additional compounds that have been prepared by mixed anhydride method using water as solvent:

| Compound | Yield % | Melting Point OC | Boiling Point OC |
|---|---|---|---|
| Esters | | | |
| Methyl benzoate | 73 | — | 197–9 |
| Benzyl myristate | 90 | | 232–5/15 mm. |
| Dodecyl 12-hydroxy-stearate | 97 | 61–2 | — |
| Methyl stearate | 92 | 38–9 | — |
| Amides | | | |
| Dihydrocinnanamide | 54 | 90–2 | — |
| Dodecylamide | 95 | 98–9 | — |
| 12-Hydroxystearamide | 90 | 129–32 | — |
| Nonanoylamide | 80 | 98–9 | — |
| Palmitamide | 94 | 105–7 | — |
| Myristylamide | 98 | 103–5 | — |
| Hexdecanamide | 51 | 101–3 | — |
| Decanamide | 82 | 106–8 | — |
| Stearamide | 93 | 107–8 | — |
| N-Substituted amides | | | |
| Dodecanoylanilide | 70 | 74–5 | |
| 2-n-octanoylamido benzothiazole | 72 | 114–15 | |

I claim:

1. A process for the preparation of an ester or an amide which comprises contacting an acid with an alkyl chloroformate in an aqueous medium that is 100% water to form an anhydride and thereafter contacting said anhydride with an alcohol to form an ester or an amine to form an amide.

2. A process as defined in claim 1 wherein an ester is prepared.

3. A process as defined in claim 1 wherein an amide is prepared.

4. A process for making an ester of the formula:

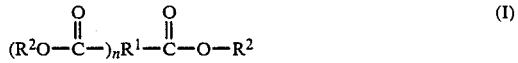

wherein $R^1$ is selected from the group consisting of straight and branched chain alkyl or hydroxylalkyl of from 2–30 carbons; straight and branched chain alkenyl or hydroxyalkenyl of from 2-30 carbon atoms; alkaryl; aralkyl; aryl; of cycloalkyl from 5 to 7 carbons; alkarylene; alkylene; and arylene; $R^2$ is independently selected from the group consisting of straight and branched chain alkyl or hydroxyalkyl of from 1 to 30 carbon atoms; straight and branched chain alkenyl or hydroxyalkenyl of from 1 to 30 carbons; cycloalkyl of from 5 to 7 carbons; alkaryl; aralkyl and aryl; and n is 1 or 0; said process comprising contacting a compound of formula II:

(II)

wherein $R^1$ and n are the same as hereinabove defined with a chloroformate of the formula $ClCOOR^4$ wherein $R^4$ is alkyl of from 1 to 10 carbon atoms or aryl in an aqueous medium that is 100% water to form an anhydride of formula III:

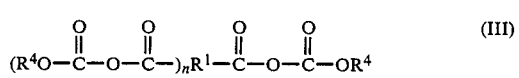
(III)

wherein $R^1$, $R^2$ and n are the same as hereinabove defined; reacting the anhydride of formula III with a compound of formula IV:

$(HO-)_n R^2-OH$ (IV)

wherein $R^2$ and n are the same as hereinabove defined to form a compound of formula I which is subsequently recovered from the reaction mixture.

5. A process as defined in claim 4 wherein n is 0.

6. A process as defined in claim 5 wherein $R^1$ is $CH_3(CH_2)_6-$ and $R^2$ is benzyl.

7. A process as defined in claim 5 wherein $R^1$ is $CH_3(CH_2)_{14}-$ and $R^2$ is cetyl.

8. A process as defined in claim 5 wherein $R^1$ is $CH_3(CH_2)_4-$ and $R^2$ is methyl.

9. A process as defined in claim 5 wherein $R^1$ is phenyl and $R^2$ is benzyl.

10. A process as defined in claim 5 wherein $R^1$ is phenyl and $R^2$ is methyl.

11. A process as defined in claim 5 wherein $R^1$ is $CH_3(CH_2)_{12}-$ and $R^2$ is benzyl.

12. A process as defined in claim 5 wherein $R^1$ is $CH_3(CH_2)_5CHOH(CH_2)_{10}-$ and $R^2$ is dodecyl.

13. A process as defined in claim 5 wherein $R^5$ is $CH_3(CH_2)_{16}-$ and $R^2$ is methyl.

14. A process for making amide of the formula:

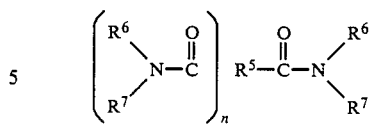

wherein $R^5$ is selected from the group consisting of straight and branched chain alkyl, aminoalkyl or hydroxyalkyl of from 1 to 30 carbons; straight and branched chain alkenyl, aminoalkyenyl or hydroxyalkenyl of from 1 to 30 carbons; aryl; cycloalkyl of from 5 to 7 carbons; alkylene; arylene; $R^6$ and $R^7$ may be the same or different and are independently selected from the group consisting of hydrogen; straight and branched chain alkyl, hydroxyalkyl, aminoalkyl, alkyl of from 1 to 30 carbon atoms, straight and branched chain alkenyl or hydroxyalkenyl of from 1 to 30 carbon atoms, aryl; cyclobenzothiazole; and n is 0 or 1 said process comprising contacting a compound of the formula:

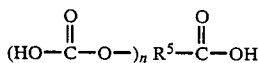

when $R^5$ and n are as hereinabove defined with a chloroformate of the formula $ClCOOR^4$ when $R^4$ is alkyl of from 1 to 10 carbon atoms or aryl in an aqueous medium that is 100% water to form an anhydride of the formula:

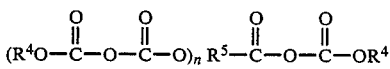

wherein $R^4-O$, $R^5$ and n are the same as hereinabove described; which is reacted wtih a compound of the formula:

wherein $R^6$, $R^7$ and n are the same as hereinabove defined and thereafter recovering said reaction product.

15. A process as defined in claim 14 wherein n is O.

16. A process as defined in claim 15 wherein $R^5$ is $CH_3-(CH_2)_6-$ and $R^6$ and $R^7$ are hydrogen.

17. A process as defined in claim 15 wherein $R^5$ is $CH_3(CH_2)_4$ and $R^6$ is hydrogen and $R^7$ is 2-benzotriazole.

18. A process as defined in claim 15 wherein $R^5$ is $CH_3(CH_2)_{12}-$ and $R^6$ is hydrogen and $R^7$ is 3-dimethylaminopropyl.

* * * * *